US00PP11277P

United States Patent [19]

Gilford et al.

[11] Patent Number: Plant 11,277

[45] Date of Patent: Mar. 7, 2000

[54] STRAWBERRY PLANT NAMED 'CAPTIVA'

[75] Inventors: Kristie L. Gilford, Dover, Fla.; Bruce D. Mowrey, La Selva Beach, Calif.; Arturo Fuentes, Sydney, Fla.; Joseph I. Espejo, Jr., Watsonville; Thomas M. Sjulin, Aromas, both of Calif.

[73] Assignee: Driscoll Strawberry Associates, Inc., Watsonville, Calif.

[21] Appl. No.: 08/858,843

[22] Filed: May 19, 1997

[51] Int. Cl.[7] ..... A01H 5/00

[52] U.S. Cl. ..... Plt./209

[58] Field of Search ..... Plt./49, 48, 209, Plt./208

[56] References Cited

U.S. PATENT DOCUMENTS

| | | | |
|---|---|---|---|
| P.P. 1,745 | 8/1958 | Lang | Plt./49 |
| P.P. 8,649 | 3/1994 | Sjulin | Plt./48 |
| P.P. 9,909 | 6/1997 | Ackerman et al. | Plt./49 |

*Primary Examiner*—Howard J. Locker
*Assistant Examiner*—Kent L. Bell
*Attorney, Agent, or Firm*—Pennie & Edmonds LLP

[57] ABSTRACT

This invention relates to a new and distinct variety of strawberry plant named 'Captiva', botanically identified as *Fragaria×ananassa* Duch. The closest known variety is 'Key Largo'. The new variety is partially everbearing. The new variety is characterized from 'Key Largo' by its flat plant habit, dense plant density, rounded teeth on the terminal leaflet, short fruiting trusses, light red fruit flesh, and very early to early to season of harvest.

3 Drawing Sheets

BACKGROUND OF THE INVENTION

The new variety of strawberry plant was selected as a seedling in a controlled breeding plot at the Garrison Farm in Hillsborough County, Fla., U.S.A., on or about December 1993. The new variety originated as a result of a controlled cross between the strawberry plants 'Key Largo', U.S. Plant Pat. No. 8,649, and Driscoll Strawberry Associates, Inc. variety named 'L1' (unpatented) in an on-going breeding program. The seedling of the new variety was grown and asexually propagated by stolons at the nursery of Driscoll Strawberry Associates, Inc., in Shasta County, Calif. The new variety was further asexually propagated and extensively tested. This propagation and testing has demonstrated that the combination of traits disclosed herein which characterize the new variety are fixed and retained true to type through successive generations of asexual reproduction.

SUMMARY OF THE INVENTION

The present invention relates to a new and distinct strawberry variety. The varietal denomination of the new variety is 'Captiva' (formerly known as 'DX-1'). The variety is botanically identified as *Fragaria×ananassa* Duch. Among the characteristics which distinguish the new variety from other varieties of which we are aware are a combination of traits which include plant habit and density, the shape of the teeth on the terminal leaflet, fruiting trusses, fruit flesh color and season of harvest.

COMPARISON TO CLOSET VARIETIES

The variety which we believe to be closest to 'Captiva' from those known to us is 'Key Largo' (U.S. Plant Pat. No. 8,649). There are several characteristics of the new variety that are different from, or not possessed by 'Key Largo'. For example, the plant habit of 'Captiva' is flat, while that of 'Key Largo' is flat globose. The plant density of 'Captiva' is medium dense to dense, While that of 'Key Largo' is open to medium dense. The teeth on the terminal leaflet of 'Captiva' are rounded while those of 'Key Largo' are obtuse. The fruiting trusses of 'Captiva' are short, while those of 'Key Largo' are long. The fruit flesh of 'Captiva' is light red, while that of 'Key Largo' is medium red. Lastly, the season of harvest for 'Captiva' is very early to early, while that of 'Key Largo' is early to mid-season.

Regarding isozyme analysis, the phosphoglucoisomerase (PGI) isozyme banding pattern for 'Captiva' is A2 while that for 'Key Largo' is A1. The leucine aminopeptidase (LAP) isozyme banding pattern for 'Captiva' and 'Key Largo' is B3. The phosphoglucomutase (PGM) isozyme banding pattern for 'Captiva' is C2 while that for 'Key Largo' is C4. All isozyme analyses were conducted using leaf tissue. See *J. Amer. Soc. Hort. Sci.* 106:684 (1981).

TABLE 1

Isozyme Analysis for 'Captiva' and 'Key Largo'

| | Cultivar | |
|---|---|---|
| Locus | 'Captiva' | 'Key Largo' |
| PGI | A2 | A1 |
| LAP | B3 | B3 |
| PGM | C2 | C4 |

The 'Key Largo' isozyme data is from U.S. Plant Pat. No. 8,649.

BRIEF DESCRIPTION OF THE ILLUSTRATIONS

The accompanying photographs show typical specimens of the new variety, including fruit, foliage and flowers, in color as nearly true as it is reasonably possible to make in color illustrations of these characteristics.

DESCRIPTION OF THE NEW VARIETY

Figure 1:
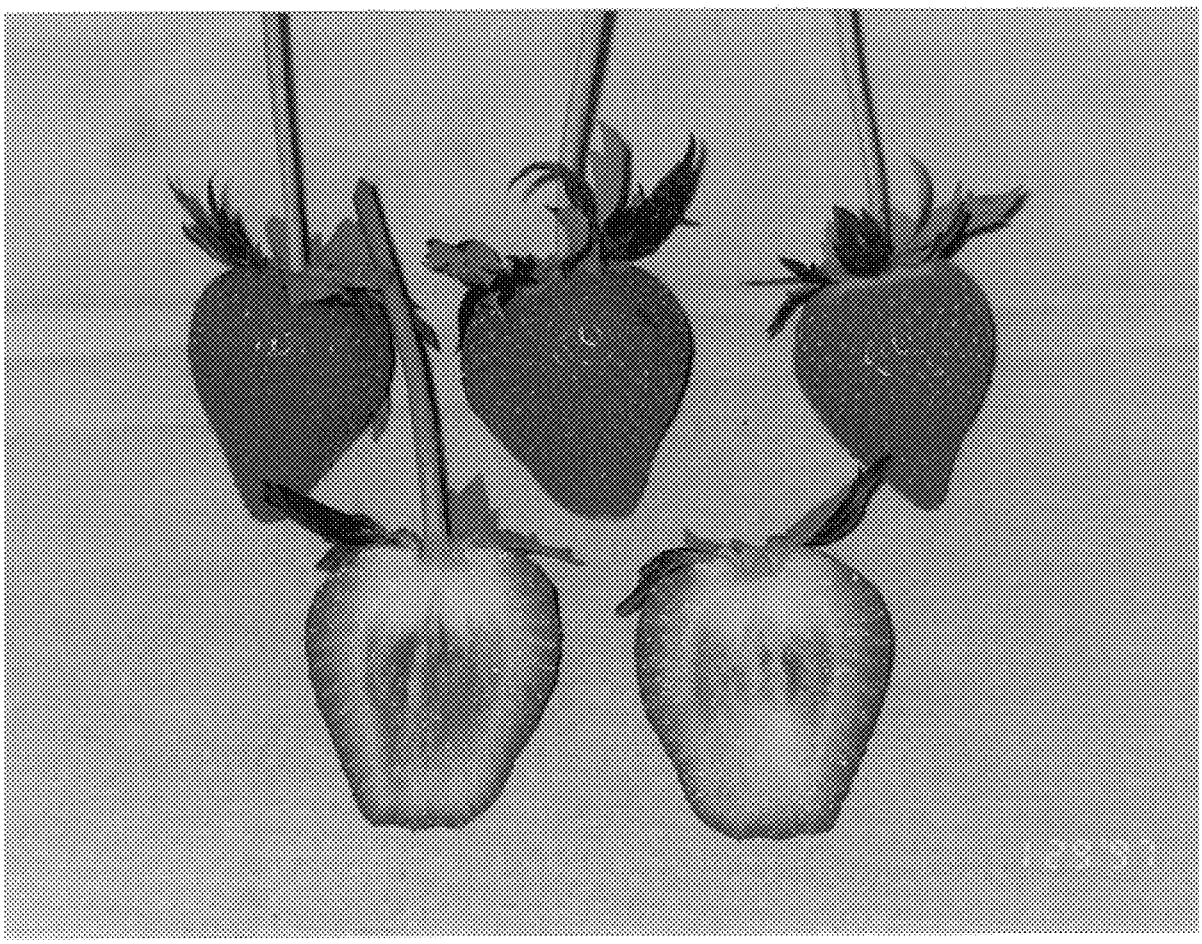
FIG. 1 shows typical whole fruit and the fruit in longitudinal section, illustrating the typical flesh and flesh coloration, core and shape of the new variety.
Figure 2:
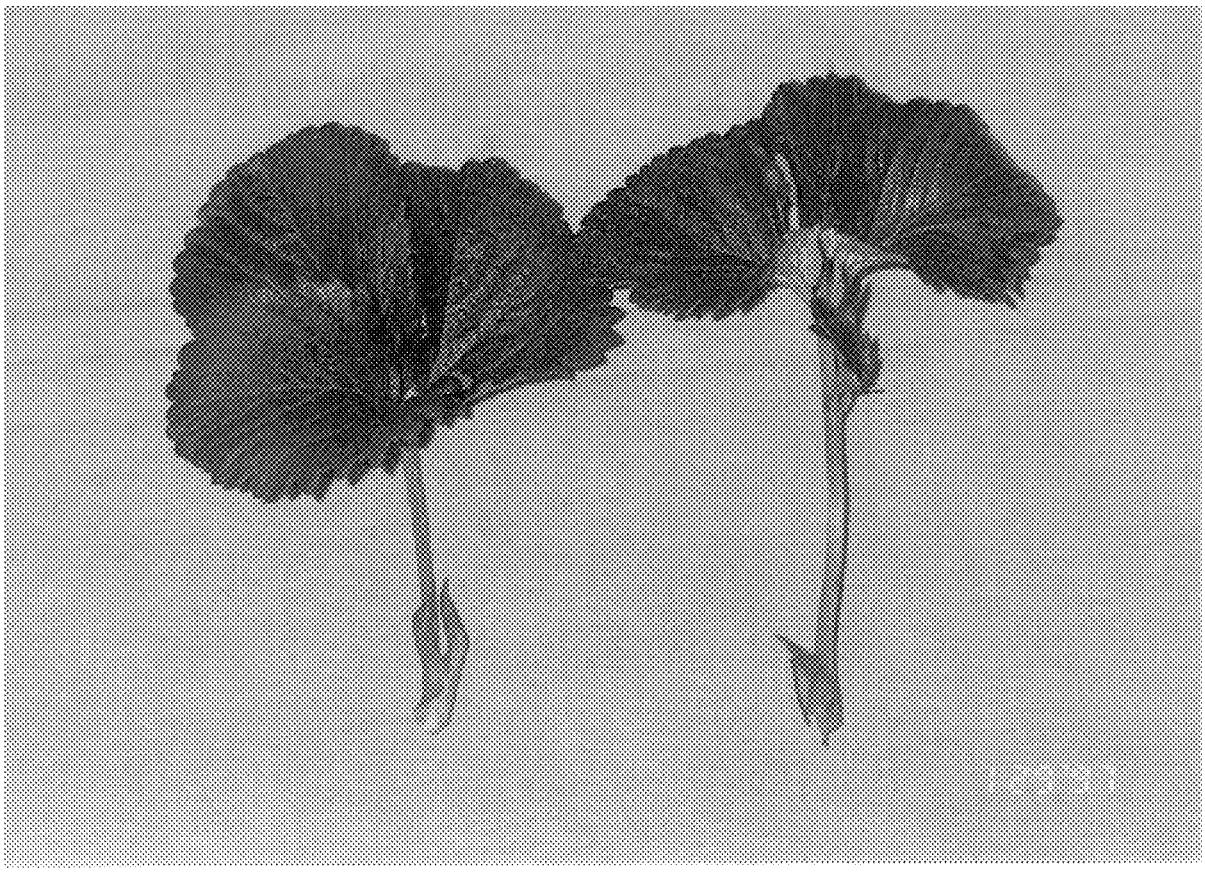
FIG. 2 shows the upper surface of two typical folioles of the new variety.
Figure 3:
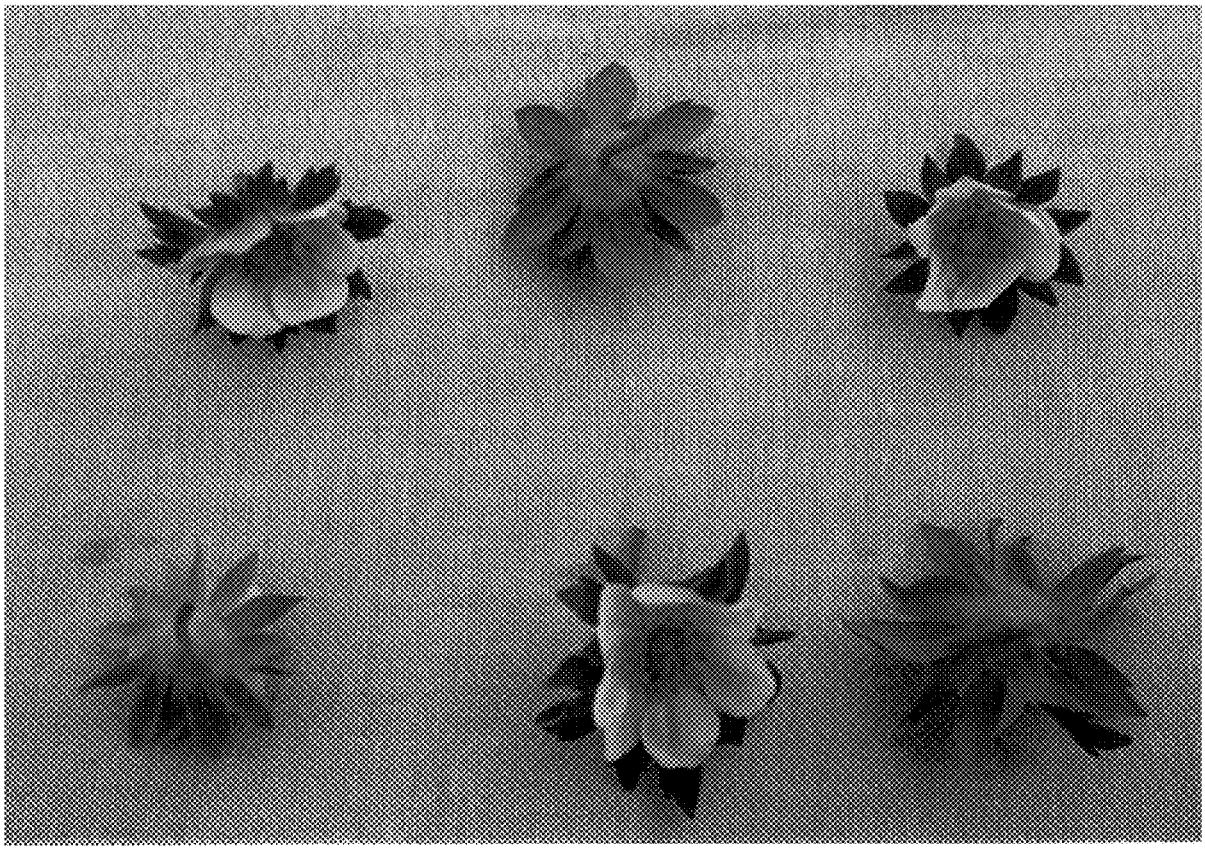
FIG. 3 shows the flowers and reproductive organs of the new variety, as well as the size and position of the petals and sepals.

The following detailed description of the new variety is based upon observations taken of plants and fruit grown in experimental test plots in 1997 at the Garrison Farm in Hillsborough County, Fla., U.S.A. The plant material was planted on Oct. 9, 1996, and 'Captiva' was grown in a forcing system during the winter. Observations of 'Captiva' and 'Key Largo' were taken in a side-by-side comparison in January 1997. Additional measurements were taken in Florida during the 1997-98 and 1998-99 growing seasons. This description is in accordance with UPOV terminology. Color designations, color descriptions, and other phenotypical descriptions may deviate from the stated values and descriptions depending upon variation in environmental, seasonal, climatic and cultural conditions. Colors are described using standard Munsell Notation.

Propagation

The new variety is principally propagated by way of stolons. Although propagation by stolons is presently preferred, other known methods of propagating strawberry plants may be employed.

Characteristics of the New Variety

The following information is provided to describe the new variety.

Plant: The plant density of 'Captiva' is medium dense to dense and has a flat plant habit with medium vigor. Specifically, at fruiting the average height and average width of a plant 'Captiva' are 12.6 cm and 32.8 cm, respectively.

Leaves: The upperside of the leaves are dark green with a Munsell color rating of 1.5G 2.8/7.4. The underside of the leaves are gray-green which is not included on the Munsell color cascade.

The leaf profile is slightly concave to flat. The leaves have medium interveinal blistering. Plants have three leaflets only. The leaf shape is oval to rounded. The terminal leaflet margin profile is revolute and the length-to-width ratio is longer than broad. The shape of the base of the terminal leaflet is obtuse and the teeth are rounded. The shape of the terminal leaf apex is obtuse to rounded. The average terminal leaflet width of 'Captiva' is 7.4 cm. The average terminal leaflet length of 'Captiva' is 8.2 cm. The venation of the leaflets is pinnate. The leaves have weak glossiness.

The petiole has sparse pubescence and the pose of the hairs is upwards. The average petiole length of 'Captiva' is 6.8 cm. The average petiole diameter is 0.4 cm. The Munsell color rating for petiole color of 'Captiva' is 3.3 GY 5.0/8.8. The average frequency of the bracts is 0.4 (40% of petioles). The bracts occur most frequently in pairs. The bracts are ovate in shape with serrate margins. The margins of the bracts are frequently fused producing a tube. The average bract length is 2.35 cm. The average bract width is 1.81 cm. The shape of the stipule is lanceolate. The average stipule length is 3.7 cm. The average stipule width is 2.0 cm.

Stolons: 'Captiva' has few to a medium number of stolons of medium thickness, medium to strong anthocyanin coloration and medium pubescence.

Inflorescence: The positioning of the inflorescence is beneath the foliage. The flowers are medium to large in size. The average flower diameter is 3.6 cm. The aspect or appearance of the flower of 'Captiva' is the typical look and shape of the species. The anther color is yellow with a Munsell color rating of 5.4Y 8.2/14.2. The average petal length is 1.4 cm. The average petal width is 1.5 cm. The petal color is white which is not included on the Munsell Color Cascade. The texture of the petals is smooth.

The diameter of the calyx is larger than the corolla. The average calyx diameter is 4.8 cm. On secondary flowers, the diameter of the inner calyx is from smaller to the same size as the outer calyx. On secondary flowers with 5 to 6 petals, the petals are overlapping. The petal length on secondary flowers is as long as the width.

The fruiting trusses are short in length and the attitude at first picking is prostrate. The average number of flowers per fruiting truss of 'Captiva' is 1.3. The average yield of 'Captiva' is 256g of fruit/plant as measured in the 1997-98 fruiting season. The fruiting trusses branch at the base of the inflorescence. The frequency of branching is low.

Fruit: Observations of the fruit were taken of secondary fruits on one year old plants. Strawberry plants possess a branching inflorescence, or peduncle, having a primary (first) flower which is the largest and secondary flowers which are on the lateral branches. "Secondary fruit" are those that develop from secondary flowers which develop from lateral buds on the peduncle. One year old plants are those which are in their first year in the fruiting field. The fruit are predominantly conical in shape and are longer than broad. The fruit are large in size. The average length and diameter of the fruit are 4.0 cm and 3.0 cm, respectively. The average weight of the fruit is 19.4g/berry as measured in the 1997-98 fruiting season. There is a moderate difference in shapes between the primary and secondary fruits. The band without achenes is narrow. The fruit surface has a weak unevenness. The average length and average width of the primary fruit are 4.7 cm and 4.2 cm, respectively. The length/width ratio of the primary fruit is 1.12. The characteristics of the primary fruit are not substantially different from those of secondary fruit.

Fruit Color: The skin color is dark red with a Munsell color rating of 6.3R 2.5/8.9 and strong glossiness. The skin color of the fruit is even.

The insertion of the achenes are level with the surface of the fruit. The achenes are yellow (Munsell color rating 4.OY 8.3/14.0) but darken to a red color when exposed to sunlight. (Munsell color rating 6.7R 3.5/13.1).

The calyx is inserted level with the fruit and the pose of the calyx segments is reflexed. The calyx diameter is much larger than the fruit diameter. The adherence of the calyx to the fruit is strong.

The fruit flesh is firm when fully ripe. The color of the fruit flesh is light red with a Munsell color rating of 8.4R 4.0/15.6. The flesh color is uneven to slightly uneven.

The fruit has strong sweetness, with medium acidity and fine texture.

The time of flowering when 50% of the plants are at first flower is very early to early. When the 'Captiva' variety was planted in Florida in early October, the plants began flowering in late October to early November.

The harvest maturity when 50% of the plants have ripe fruit is very early to early. For 'Captiva' planted in Florida in early October, 50% of the plants possessed ripe fruit in late November. The 'Captiva' is a partially everbearing variety. Partially everbearing varieties are everbearing (fruit two or more times per season) in cool coastal climates, such as in coastal California, but otherwise stop producing fruit in the summer under warm temperatures.

Chilling Requirements: 'Captiva' has only been tested extensively in Florida in a green plant system. In this system the plants are transplanted from the nursery to the fruiting field with the leaves intact. Chilling is not a requirement in this system.

Day length responsiveness: 'Captiva' is a short day or June bearing plant.

Resistance to Stress

The new variety 'Captiva' is moderately resistant to drought and high temperatures.

Disease Resistance and Susceptibility

The 'Captiva' fruit is moderately resistant to decay by Botrytis fruit rot.

The 'Captiva' variety is susceptible to injury by the two-spotted spider mite (*Tetranychus urticae*), *Tarsonemus pallidus, Aphelencoides fragariae,* Aphis spp., and lygus bug (*Lygus hesparus*).

What is claimed is:

1. A new and distinct variety of strawberry plant, substantially as shown and described.

* * * * *